(12) United States Patent
Bischoff et al.

(10) Patent No.: US 10,401,224 B2
(45) Date of Patent: Sep. 3, 2019

(54) METHOD FOR ASCERTAINING TEXTURE PARAMETERS OF A PAINT

(71) Applicant: BASF Coatings GmbH, Münster (DE)

(72) Inventors: Guido Bischoff, Drensteinfurt (DE); Martin Schmitz, Drensteinfurt (DE); Donald R Baughman, Perrysburg, OH (US)

(73) Assignee: BASF Coatings GmbH, Münster (DE)

( * ) Notice: Subject to any disclaimer, the term of this patent is extended or adjusted under 35 U.S.C. 154(b) by 0 days.

(21) Appl. No.: 15/771,577

(22) PCT Filed: Oct. 27, 2016

(86) PCT No.: PCT/EP2016/025131
§ 371 (c)(1),
(2) Date: Apr. 27, 2018

(87) PCT Pub. No.: WO2017/071824
PCT Pub. Date: May 4, 2017

(65) Prior Publication Data
US 2019/0078936 A1    Mar. 14, 2019

Related U.S. Application Data

(60) Provisional application No. 62/247,837, filed on Oct. 29, 2015.

(30) Foreign Application Priority Data

Oct. 29, 2015   (DE) .......... 10 2015 118 551

(51) Int. Cl.
*G01J 3/46*    (2006.01)
*G06N 3/02*    (2006.01)
(Continued)

(52) U.S. Cl.
CPC .......... *G01J 3/463* (2013.01); *G01J 3/46* (2013.01); *G01J 3/462* (2013.01); *G01J 3/504* (2013.01);
(Continued)

(58) Field of Classification Search
CPC ........ G01J 3/46; G01J 3/50; G01J 3/02; G01J 3/524; G01J 3/51
(Continued)

(56) References Cited

U.S. PATENT DOCUMENTS 6,714,924 B1    3/2004    McClanahan
7,804,597 B2 *  9/2010    De Haas .......... G01J 3/46
                                              356/402

(Continued)

FOREIGN PATENT DOCUMENTS

EP    2161555 A1    3/2010
JP    2013-047678 A    3/2013
(Continued)

OTHER PUBLICATIONS

Kirchner, et al., "Predicting and measuring the perceived texture of car paints", Proceedings of the 3rd International Conference on Appearance Predicting Perceptions, Apr. 17, 2012, pp. 25-28.
(Continued)

*Primary Examiner* — Md M Rahman
(74) *Attorney, Agent, or Firm* — Armstrong Teasdale LLP

(57) ABSTRACT

Described herein is a method for predicting visual texture parameters of a paint having a known paint formulation. The visual texture parameters of the paint are determined using an artificial neural network on the basis of a number of color components used in the known paint formulation. The method includes determining a value of at least one characteristic variable describing at least one optical property using a physical model for the known paint formulation. The
(Continued)

method also includes assigning the value to the known paint formulation, and transmitting the value to the artificial neural network as an input signal for determining the visual texture parameters. The value describes the at least one optical property for at least some of the number of color components of the known paint formulation. The method further includes training the neural network using a plurality of color originals each having a respective known paint formulation.

11 Claims, 2 Drawing Sheets

(51) Int. Cl.
    *G01J 3/50*     (2006.01)
    *G06N 3/08*     (2006.01)

(52) U.S. Cl.
    CPC ............... *G06N 3/02* (2013.01); *G06N 3/084* (2013.01); *G01N 2201/1296* (2013.01)

(58) Field of Classification Search
    USPC ......................................................... 356/402
    See application file for complete search history.

(56) References Cited

U.S. PATENT DOCUMENTS

| | | |
|---|---|---|
| 2004/0073526 A1 | 4/2004 | McClanahan |
| 2007/0250273 A1* | 10/2007 | De Haas .................... G01J 3/46 |
| | | 702/22 |
| 2009/0157212 A1 | 6/2009 | McClanahan et al. |
| 2009/0213120 A1* | 8/2009 | Nisper .................... G01J 3/504 |
| | | 345/426 |
| 2014/0242271 A1 | 8/2014 | Prakash et al. |
| 2016/0321546 A1 | 11/2016 | Delespierre et al. |

FOREIGN PATENT DOCUMENTS

| | | |
|---|---|---|
| WO | 2006030028 A1 | 3/2006 |
| WO | 2012177508 A2 | 12/2012 |

OTHER PUBLICATIONS

Spehl, et al., "Application of backpropagation nets for color recipe prediction as a nonlinear approximation problem", International Conference on Neural Networks, vol. 5, Jun. 27, 1994, pp. 3336-3341.

International Search Report for International Application No. PCT/EP2016/025131, dated Jan. 30, 2017, 3 pages.

* cited by examiner

METHOD FOR ASCERTAINING TEXTURE PARAMETERS OF A PAINT

CROSS-REFERENCE TO RELATED APPLICATIONS

This application is the national stage entry of PCT/EP2016/025131, filed on Oct. 27, 2016, which claims the benefit of priority to German Patent Application No. 102015118551.2, filed Oct. 29, 2015, and U.S. Provisional Patent Application No. 62/247,837, filed Oct. 29, 2015, which are incorporated by reference in their entirety herein.

FIELD OF THE INVENTION

The present invention relates to a method for determining and/or predicting texture parameters of a paint, and also to a corresponding computer program for implementing the presented method on an arithmetic unit.

BACKGROUND

Paint finishes comprising what are called effect pigments are widespread within the automobile industry. Metallic effect pigments and interference pigments are examples of effect pigments. They endow a paint with additional properties such as changes in lightness and in shade angle-dependently, for example. This means that the lightness or shade of the paint in question changes depending on the angle from which the paint is viewed. Effect pigments result in a visually perceptible granularity or graininess (also called coarseness) and to sparkle effects ["Coloristik für Lackanwendungen (Farbe and Lack Edition)", Tasso Baurle et al., bound edition—Mar. 14, 2012]. These effects are also referred to as visual texture.

There are currently two techniques in use for characterizing effect paints.

The first technique uses a light source to illuminate a particular paint surface and measures the spectral reflection at different angles. From the results obtained and from the radiation function of the light source it is possible to calculate chromaticity values, e.g., CIEL*a*b* [ASTM E2194 "Standard Test Method for Multiangle Color Measurement of Metal Flake Pigmented Materials", ASTM E2539 "Standard Test Method for Multiangle Color Measurement of Interference Pigments"].

In the case of the second technique, the paint surface is photographed under defined light conditions and at defined angles. From the images it is then possible to calculate texture parameters which describe the visual texture. Examples of texture parameters are the textural values G diffuse or Gdiff (graininess or coarseness), Si (sparkle intensity), and Sa (sparkle area), as introduced by the company Byk-Gardner ["Beurteilung von Effektlackierungen, Den Gesamtfarbeindruck objektiv messen" (Assessment of effect finishes—objective measurement of overall color impression), Byk-Gardner GmbH, JOT 1.2009, vol. 49, issue 1, pp. 50-52]. The textural values of Byk-Gardner are determined from gray stage images. It is also possible for textural values to be determined individually for different color channels of a color image—e.g., for a red channel, a green channel, and a blue channel.

In a color formula calculation, an attempt is made to reproduce a color original by means of a mixture of available colorants, by calculating the concentrations of colorant required. A necessary precondition in color formula calculation is the prediction of the spectral reflection of a respective color formulation. A color or paint formulation or formula, for the purposes of the present disclosure, refers to a specific composition of different colorants and/or color components with defined respective colorant concentrations. This means that a color or paint formulation defines a kind of list of items—that is, a quantitative composition of a paint comprising its individual components, i.e., its individual color components.

One common method is to calculate reflection spectra on the basis of physical models (e.g., Kubelka-Munk equation). In this process, optical constants are determined for each colorant by means of the physical model, on the basis of actual applications of known colorant compilations. These optical constants are model-dependent and characterize the colorant in question. Examples of the optical constants are the parameters K and S of the Kubelka-Munk equation, which describe the absorption (parameter K) and scattering (parameter S). Where the optical constants are determined for all colorants to be used, the spectral reflection of any desired color formulation can be calculated using the physical model.

For the mixing of a paint, such as a colored paint for a vehicle, for example, it is general practice to use color formulations which indicate a mixing ratio of respective color components to one another in order to generate a paint having a desired color effect. For replication of an effect paint, such as a metallic paint, for example, not only the spectral reflection properties but also objective texture parameters, such as graininess or coarseness, for example, are required as a description of the optical properties of a corresponding shade original.

For the prediction of visual texture parameters of such effect paints on the basis of formula data, as mentioned above, regression-based processes are traditionally used. In such processes, characteristic parameters, such as concentration of pigment types present in a paint, for example, such as of metallic effect pigments and interference pigments, for example, a spectral reflection, predicted by a physical model, or variables derived from respective optical constants of the physical model are calculated for a paint formulation. A linear combination of these parameters then forms a statistical model for the prediction of the visual texture parameters. The coefficients of the linear combination are determined by regression analysis, as described in Kirchner, Ravi "Predicting and measuring the perceived texture of car paints", Proceedings of the 3rd international conference on Appearance "Predicting Perceptions", Edinburgh, Apr. 17-19, 2012.

Another way of predicting the visual texture parameters of an effect finish is by using artificial neural networks.

One neural network for use in this context is based on a learning process referred to as backpropagation. The neurons of the neural network are arranged in layers. These include a layer with input neurons (input layer), a layer with output neurons (output layer), and one or more inner layers. The output neurons are the visual texture parameters of the paint formulation that are to be predicted, in other words the aforementioned parameters of Si, Sa, and Gdiff.

To predict the spectral reflection of an effect paint formulation, as already mentioned, a physical model is used.

In a first known solution approach, input parameters or input neurons used for the neural network are the concentrations of the colorants or color components used in the particular paint formulation under consideration, and the reflection spectrum as predicted by a physical model.

The use as input parameters of concentrations of colorants to be employed has a number of disadvantages, however:

The number of colorants in a paint series is very high, and so the number of neurons in the input layer of the neural network is very large. Precise prediction of the texture parameters requires a large quantity of training data.

In the event of any change in the paint series, the neural network must be redefined, retrained, and retested. This implies considerable administration effort and expense.

The effort and expense of adding a further colorant to a paint series is great: in the case of new colorants, numerous mixtures must be produced as a basis for training the neural network.

Known from the U.S. Pat. No. 6,714,924 B1 is a method and apparatus for color matching wherein neural networks are employed. Here, the color of a color standard is expressed by color values, with the input signals of the neural network used being related to paint bases. Furthermore, weighted connections are provided between the input nodes of the input layer of the neural network and the output nodes of the output layer of the neural network. Initial weighted connections here determine the respective contribution of the paint bases of the input layer to each output color component.

Known from US 2009/0157212 A1 is a method and a system for determining a paint formulation comprising an effect pigment. The system comprises a roughness measuring instrument which must be placed adjacent to the painted surface, such as that of a vehicle, for example, with a technician comparing the display with the painted surface in order to determine the roughness of the effect pigment.

SUMMARY

Presented against this background is a method for determining or predicting visual texture parameters of a paint having a known paint formulation, wherein visual texture parameters of the paint are determined or predicted by means of an artificial neural network on the basis of a number of color components used or to be used in the paint formulation, where a value of at least one characteristic variable describing at least one optical property is determined by means of a physical model for the known paint formulation, is assigned to the known paint formulation, and is transmitted to the artificial neural network as an input signal for determining or predicting the visual texture parameters, where the value determined and assigned to the known paint formulation describes the at least one optical property for at least some of the number of color components of the paint formulation, where color originals each with a known paint formulation are used for training the neural network, and, for each of the color originals, their respective visual texture parameters are measured and are assigned to a value of the at least one characteristic variable that is determined or calculated for the corresponding respective paint formulation and that describes the at least one optical property for that respective paint formulation.

DETAILED DESCRIPTION

Figure 1:
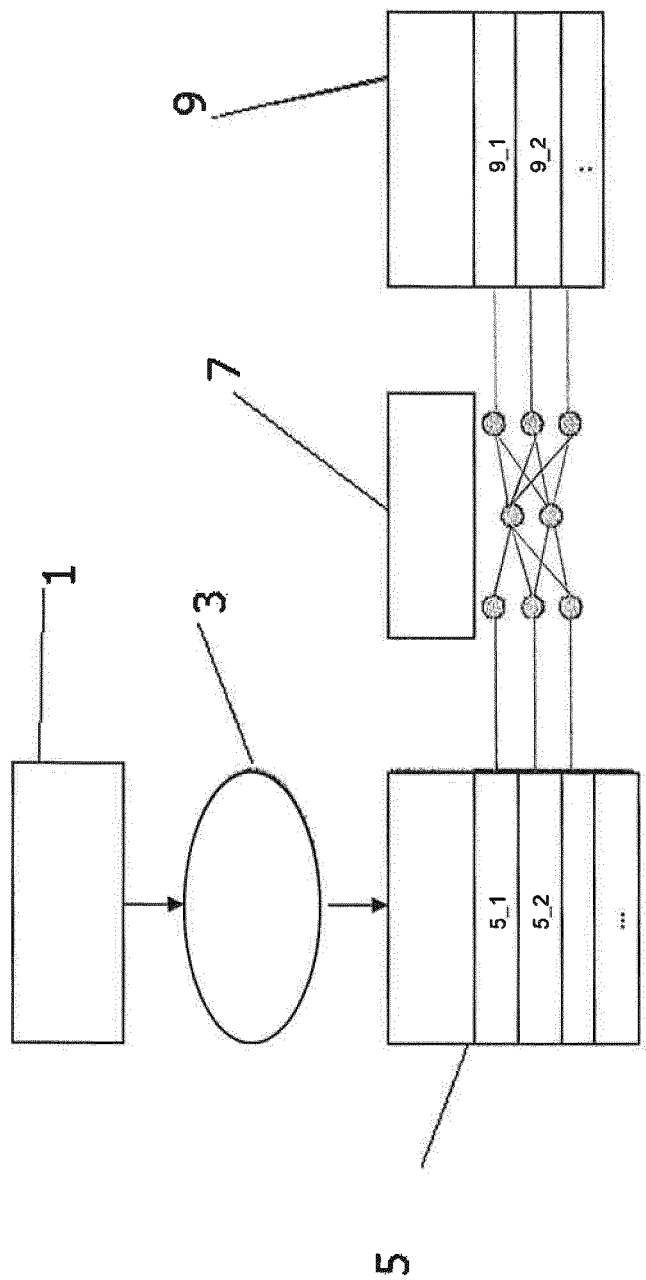
FIG. 1 shows a schematic overview of one embodiment of the method of the invention.

The phrase "a value of at least one [ . . . ] characteristic variable" is "transmitted as at least one input signal" to the neural network is intended in the context of the present description to mean that not only the value of the characteristic variable itself but also a variable determined on the basis of this value of the characteristic variable may serve as input signal and is provided to the neural network.

"A known paint formulation" means a color formula with known concentrations of color components comprised and used therein.

In the text below, the terms "value of a characteristic variable" and "characteristic variable" are used synonymously with one another. This means that in the text below, "value of the at least one characteristic variable" and "the at least one characteristic variable" should be understood synonymously. The same is true of "values of the visual texture parameters" and "visual texture parameters".

Embodiments of the invention are evident from the description and the dependent claims.

The method presented serves in particular for determining visual texture parameters of a paint having a known paint formulation by means of a neural network which is based on a learning process referred to as backpropagation. Backpropagation here should be understood as a generic term for a supervised learning process with error feedback. There are a variety of backpropagation algorithms: e.g., Quickprop, Resilient Propagation (RPROP). This process uses a neural network comprising at least three layers: a first layer with input neurons, an nth layer with output neurons, and n-inner layers, where n is a natural number greater than 2. In such a network, the output neurons serve to predict the visual texture parameters of the respective paint or corresponding paint formulation.

In the context of the present description, the terms "input signal", "input component", "input variable", and "input neuron" are used synonymously.

Provision is made in particular for respective texture parameters of the paint to be determined, by means of the neural network provided in accordance with the invention, on the basis of at least one characteristic variable, with a value of the at least one characteristic variable, or the at least one characteristic variable, being derived or determined, respectively, from at least one optical constant of at least some of the number of color components of the paint formulation or of the paint.

In a possible embodiment, the value of the at least one characteristic variable is calculated from at least one respective optical constant of all color components of the paint formulation. This means that the at least one optical constant is calculated in each case by means of a physical model for all color components of the paint formulation, and the value of the at least one characteristic variable of the paint formulation is determined or calculated on the basis of the respective optical constants of all color components of the paint formulation.

Visual texture parameters in the context of the present invention mean parameters, particularly data relating to sparkle effect, graininess or coarseness of a paint, such as, for example, Si, Sa or Gdiff. As already described at the outset, Si ("sparkling intensity") and Sa ("sparkling area") are parameters introduced by Byk-Gardner for describing the sparkle effect of a paint. The parameters are determined from series of images recorded under direct aligned illumination. Gdiff ("graininess diffuse") is a parameter introduced by Byk-Gardner for describing the graininess. The parameter is determined from an image recorded under diffuse illumination. The respective images of a respective paint surface are recorded using appropriate cameras which are configured to record images under defined illumination. The cameras are in general each part of a spectrometer.

An optical property in the context of the present disclosure means a property of a paint, or a value for describing a property of the paint, which affects the light impinging on the paint or on a corresponding paint surface—thus, for example, the extent to which this light is absorbed or reflected and, if reflected, how it is reflected.

A neural network in the context of the invention presented refers to an artificial neural network for determining and/or predicting visual texture parameters of a paint formulation of a paint, more particularly of an effect paint, where the neural network is based on backpropagation. In this system, input variables or signals of the neural network evaluated are intermediate variables determined by means of a physical and/or mathematical model from a respective paint formulation. These include, in particular, the optical constants assigned to the respective paint formulation, and also, in a further embodiment, the reflection parameters calculated from these constants.

Since the neural network provided in accordance with the invention has no direct link to the individual color components of the paint, the neural network provided in accordance with the invention is less complex in its definition than the neural networks used for this purpose to date in the prior art. While the training data used in the prior art for a neural network were based on formula data, i.e. on different concentrations to each of the approximately 80 to 250 color components, the training data for use in accordance with the invention are based on optical properties or data for different known paint formulations. Differentiation therefore no longer takes place between the specific color components and their respective concentrations, but instead between the different optical behaviors they produce. Since these optical behaviors can be described by fewer characteristic variables than the number of different color components, the neural network is less complex and therefore requires fewer training data.

Furthermore, the system is substantially more tolerant or less sensitive to changes in the color components, i.e., in the case of omission, change or addition of one or more of the color components available, there is no need for the neural network to be reconfigured (change in the layer for the input signals) and retrained.

A color component in the context of the invention presented is understood to mean a base component of a paint or of a corresponding paint formulation, such as a color pigment or a quantity of flakes for generating a sparkle effect, for example. The terms "color component" and "colorant" are to be used synonymously.

An input signal in the context of the invention presented means at least one value which serves as a basis for determining respective texture parameters of a paint formulation by means of the neural network provided in accordance with the invention.

To train the neural network provided in accordance with the invention, all that is needed is information concerning optical properties providing a basis for a respective characteristic variable of respective color components of color originals with known paint formulation in each case; for each of these color originals, their respective texture parameters are subjected to measurement and are assigned to the respective characteristic variable or the respective value of the characteristic variable determined for the particular color original. Then, with knowledge of the at least one characteristic variable or of the value of the at least one characteristic variable of a paint formulation under consideration, it is possible, by means of the neural network, to predict or determine the visual texture parameters of the paint formulation. If the visual texture parameters of other paint formulations are already known, the functioning of the neural network can also be verified repeatedly and adapted where necessary in order to achieve as precise as possible a prediction of the visual texture parameters.

The method presented is especially suitable for calculating texture parameters of a given paint formulation that can then be used in turn, within existing formula algorithms for the paint formulation, more particularly for an effect paint, as quality information.

In one possible embodiment of the method presented, provision is made for a spectral reflection of the paint that is calculated by means of a physical model to be included as an input signal. Account may be taken of absorption and/or scattering, optionally split into forward scattering and backward scattering of the paint when determining the input signal. It is also conceivable to take account of an average variable of flakes that are used in the known paint formulation, and also of a surface structure property which distinguishes between flat effect pigments (e.g., "silver dollars") and coarse effect pigments (e.g. "cornflakes") and a variable which describes average orientation of the effect pigments in relation to a particular paint surface. A transmission coefficient of the paint, situated in general at between 0 and 1, may likewise be taken into account when determining the input signal.

Through use of intermediate variables or characteristic variables, determined from the paint formulations and from the optical properties, i.e., for example, from the optical constants, of respective color components of the paint formulations, as input signals for the neural network envisaged in accordance with the invention, for determining visual texture parameters of the respective paint formulations, the neural network provided in accordance with the invention may be defined and/or trained very generally. This means that in contrast to the specific training of a neural network to a fixed number of color components, producing a very rigid and specific embodiment of a particular neural network, a generalized training may take place on the basis of optical properties of the respective paint formulations. The effect of a generalized training based on the optical properties is to produce a very universal neural network which is not adapted specifically to a fixed number and selection of color components but can instead be used without additional training even in the event of changeover, omission or replacement of respective color components, in order to predict respective texture parameters of a given paint formulation.

By using input signals determined on the basis of optical properties for the neural network envisaged in accordance with the invention, there is a considerable reduction in the effort and expenditure involved in training the neural network, as compared with the cost and complexity of training for a neural network based on concentrations of respective color components of paint formulations known accordingly. Whereas, depending on the nature and number of respective color components, there is a multiplicity of parameters to be taken into account in the case of training on the basis of concentrations of respective color components, only a relatively small number of parameters are needed in the case of use of input signals determined on the basis of optical properties, and the number of neurons in the input layer, i.e., in the first layer of the neural network provided in accordance with the invention, is low accordingly.

In a further possible embodiment of the method presented, in the event that respective color components of the paint are modified, replaced or removed, provision is made for the visual texture parameters to be determined by means of the at least one characteristic variable or of the corresponding value of the at least one characteristic variable even without renewed training of the neural network.

Provision is made in particular for the characteristic variable envisaged in accordance with the invention to be selected such that the neural network provided in accordance with the invention is extremely tolerant toward changes in the number or the embodiment of respective color components of a paint or of a paint formulation. For this purpose, provision is made for the characteristic variable or the optical property forming the basis of the at least one characteristic variable to be selected such that it is as far as possible abstract—that is, not directly connected to the concentrations of the respective color components of the respective paint formulation—and nevertheless is suitable for describing consequences of the color components for the visual texture parameters. One possibility of a characteristic variable of this kind is the choice of a characteristic variable based on optical constants of a particular paint formulation, such as, for example, an average—weighted by the concentration of the respective color components of the paint formulation—of the absorption component K and of the scattering component S according to the Kubelka-Munk theory, for the individual color components. Further characteristic variables are derived from the paint formulation reflection spectrum predicted by the aforementioned physical model, as for example the coordinates in the L*a*b* color space.

The characteristic variable envisaged in accordance with the invention serves as a control element for producing tolerance in the neural network provided in accordance with the invention relative to changes in the input signal of the neural network. If the characteristic variable is selected very narrowly, i.e. in a manner specifically adapted to respective color components, a corresponding neural network, in the event of changes in the color components of a respective paint, will calculate incorrect or invalid texture parameters unless the amended color components were already part of a set of training data of the neural network. If, in contrast, the characteristic variable selected is abstract, i.e., having general validity as far as possible, a corresponding neural network determines reliable texture parameters even when there are changes in the color components that were not part of the set of training data for the neural network.

In a further possible embodiment of the method presented, provision is made for the at least one characteristic variable to be determined by means of a mathematic and/or physical model on the basis of parameters, measured by means of at least one sensor, of at least one color component of the number of color components of the paint formulation.

The characteristic variable provided in accordance with the invention may of course also be determined—calculated, for example—on the basis of a measurement, such as a measurement with a spectrophotometer, by means of an intermediate step, before the characteristic variable is used as an input signal for the neural network provided in accordance with the invention. In that case the characteristic variable may itself be used as input signal or may be used for determining the input signal, via calculations by means of a physical and/or mathematical model, for example.

In a further possible embodiment of the presented method, provision is made for a set of parameters to be selected as characteristic variable that describes at least one optical property for at least some of the number of color components of the paint or of the paint formulation.

It is conceivable for the characteristic variable envisaged in accordance with the invention to comprise a multiplicity of parameters, i.e., a set of parameters. Thus, for example, an optical constant and a reflection spectrum of a respective color component may be jointly used to form the characteristic variable envisaged in accordance with the invention.

In a further possible embodiment of the presented method, provision is made for the at least one optical property described by the at least one characteristic variable to be selected from the following list of optical properties: spectral reflection of a paint or paint formulation, optical constant of at least one color component of a number of color components of the paint, reflection spectrum predicted by means of a physical model for at least one color component of the paint, absorption component K according to the Kubelka-Munk theory, scattering component S according to the Kubelka-Munk theory, and at least one optical characteristic variable calculated from the respective optical constants of the number of color components of the paint. An optical constant is, for example, an absorption coefficient, a transmission coefficient and/or a scattering coefficient.

Generally speaking, all technically appropriate details for describing optical properties of at least one color component of the number of color components of the paint are suitable for determining the value of the characteristic variable envisaged in accordance with the invention. It is envisaged in particular that for determining an optical characteristic variable calculated from the respective optical constants of the color components of the number of color components, a weighted average of the respective absorption and scattering coefficients of the color components of the paint is used, or the weighted average of the respective absorption and scattering coefficients of the color components of the paint itself is selected as characteristic variable.

In a further possible embodiment of the method presented, as characteristic variable describing an optical property, provision is made for a color space coordinate to be selected which is derived from the reflection spectrum, predicted by means of the physical model, of the at least one color component of the paint.

Color space coordinates are suitable for predicting effects of respective color components on a reflection spectrum of a respective paint. Accordingly, details of color space coordinates can also be used when determining texture parameters of a respective paint.

As derived color space coordinates, and correspondingly as input variables for the neural network provided in accordance with the invention, values to be calculated from reflection values of a color component, and generally from respective reflection values of all color components of a paint formulation, may be selected from the following list of values or a combination thereof: color space coordinates in a L*a*b* color space, color space coordinates in a red-green-blue (RGB) color space, more particularly color space coordinates in a standard red-green-blue (sRGB) color space. Furthermore, additionally or alternatively, an average reflection value (R-average) of the color components of the paint formulation and/or a flop index of the paint formulation, which indicates a lightness profile and/or color profile or respective changes therein, can be used as an input variable for the neural network.

Furthermore, as values, calculated by means of a physical model, of at least one characteristic variable of a paint formulation that describes at least one optical property, i.e., of at least one color component, in general of all color components, of the paint formulation and, correspondingly, as input variables of the neural network provided in accordance with the invention, it is possible to select values based on optical constants from the following list of values or a combination thereof: transmission coefficient, forward scattering, backward scattering, average absorption and/or average scattering according to Kubelka and Munk, and orientation or alignment of any flakes and/or luster pigments present in relation to a virtual paint surface.

It is conceivable to provide a multiplicity of different input variables for the neural network.

In a further possible embodiment of the method presented, provision is made to decide on a paint formulation for a paint by means of texture parameters predicted using the neural network for a multiplicity of mandated paint formulations, the paint formulation decided on being that whose texture parameters display the least-possible deviation from texture parameters of a mandated target paint.

By means of the method envisaged in accordance with the invention it is possible to predict texture parameters for a multiplicity of mandated paint formulations without having to produce a particular paint in accordance with the respective paint formulations. On the basis of texture parameters of the multiplicity of paint formulations it is possible to select, from the multiplicity of paint formulations, a paint formulation whose texture parameters display the least-possible deviation from texture parameters of a mandated target paint. This means that, using the method of the invention, texture parameters for a multiplicity of paint formulations can be predicted without the need for respective paints to be mixed in accordance with the respective paint formulations of the multiplicity of paint formulations, in laborious test series, then applied to metal test plates and subjected to optical measurement. Instead, using texture parameters determined by means of the method of the invention, it is possible, in an entirely virtual process, for simulation purposes, for example, in other words to simulate corresponding paints, to determine, starting from a multiplicity of mandated paint formulations, the particular paint formulation whose texture parameters display the least-possible deviation from texture parameters of a target paint.

In order to predict texture parameters of a paint on the basis of a mandated paint formulation and without having actually to produce the paint in accordance with the paint formulation, first of all, using a physical model, respective optical constants for the respective color components encompassed by the paint formulation, and/or variables calculated from color data and, from these variables, at least one characteristic variable for the paint formulation are determined and/or calculated. Factors entering the calculation of the at least one characteristic variable for the paint formulation include not only the respective optical constants of the color components but also, generally, the respective concentrations of the respective color components that are mandated by the paint formulation, as is the case, for example, with the aforementioned average value of the absorption components and of the scattering components of the individual color components according to the Kubelka-Munk model, said average value being weighted with the respective concentration of the respective color components of the paint formulation.

The method presented may be used in particular for simulating paints by carrying out a purely virtual comparison between different paints on the basis of their respective parent paint formulations, without such paints being mixed in accordance with the respective paint formulations and applied to a sample panel.

The present invention further relates to a computer program product having a computer-readable medium and, stored on the computer-readable medium, a computer program with program code means configured to execute all computer-implemented steps of the above-described method of the invention when the computer program is run on an arithmetic unit.

The computer program product presented serves in particular for carrying out the method presented, and the computer program may be stored, for example, on a computer-readable data carrier.

Further advantages and embodiments of the invention are evident from the description and the appended drawing.

It is understood that the features identified above and those yet to be elucidated below may be used not only in the particular combination indicated but also in other combinations, or on their own, without departing from the scope of the present invention.

The invention is illustrated schematically in the drawings with reference to working examples and will be described comprehensively below with reference to the drawings.

FIG. 1 shows a schematic overview of one embodiment of the method of the invention.

Figure 2:
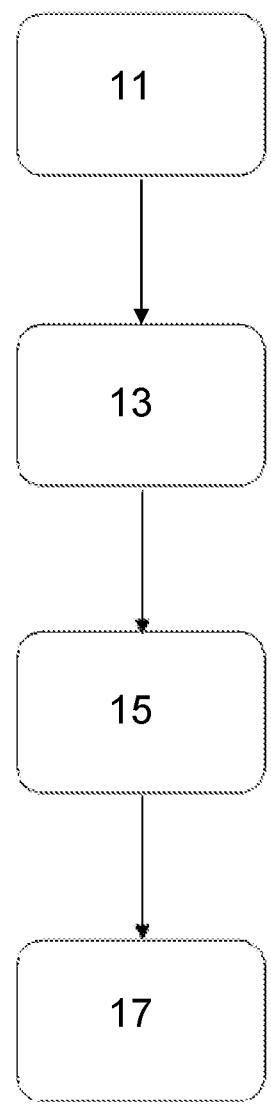
FIG. 2 shows a schematic representation of a sequence of a further possible embodiment of the method of the invention.

FIG. 2 shows a schematic representation of a sequence of a further possible embodiment of the method of the invention.

Starting from a color or paint formulation 1 for a paint, a physical model 3 is used to determine values of characteristic variables 5 which describe characteristic optical properties of the paint or of the number of color components of the paint or of at least some of the number of color components of the paint, such as, for example, a Kubelka-Munk scattering component S 5_1 and/or absorption component K 5_2.

On the basis of the values of the characteristic variables 5, one or more input signals are generated for a neural network 7 provided in accordance with the invention. The neural network assigns visual texture parameters 9, such as, for example, graininess 9_1, indicated for example by the texture parameter Gdiff, and/or sparkle effect 9_2, indicated for example by the texture parameter Si, to the input signal or input signals and, consequently, to the paint formulation 1. This assignment to be carried out by the neural network is indicated in FIG. 1 by the interwoven lines. Accordingly, by means of the neural network 7, it is possible to decide on the corresponding texture parameters 9 or their respective values, starting from the paint formulation 1.

Since the texture parameters 9 are determined or predicted on the basis of characteristic physical properties, especially optical properties, there is no need for precise training of the neural network 7 with respective concentrations of color components of the paint formulation 1. Instead, for determining the texture parameters, a knowledge of characteristic properties of the number of color components of the known color or paint formulation 1 is sufficient. This means that the neural network 7 is robust with respect to changes of color components of the paint formulation 1, and that only information concerning the characteristic physical respective color components—optionally newly added color components—is required in order to determine corresponding texture parameters 9.

FIG. 2 shows a flow diagram for implementing one embodiment of the method presented. Starting from a paint formulation 11, in an operative step 13, by means of a physical model of physical or optical properties of respective color components, such as pigments, for example, or what are called flakes, i.e. metallic sparkle components of the paint formulation 11, characteristic variables or values of characteristic variables of optical properties of the respective color components are determined and, based thereon, at least one characteristic variable or value thereof that describes at least one optical property of the overall paint formulation 11 is determined. The physical model in this case may be formed, for example, on the basis of the model according to Kubelka and Munk, as indicated on an exemplary basis by equation (1). In order to calculate the at least one characteristic variable which describes the optical properties of the paint formulation 11, optical properties of respective color components of the paint formulation are determined and are taken into account when predicting optical properties of the overall paint formulation, as a function, for example, of the concentrations of the respective color components that are mandated by the paint formulation.

$$\frac{K}{S} = \frac{c_1 k_1 + c_2 k_2 + \ldots + c_s k_s}{c_1 s_1 + c_2 s_2 + \ldots + c_s s_s} \quad (1)$$

In equation (1), "K" stands for an absorption component or absorption coefficient and "S" for a scattering component or scattering coefficient of a paint formulation, "$c_1$", "$c_2$", ..., "$c_s$" are concentrations of respective pigments of the paint formulation, "$k_1$", "$k_2$" ..., "$k_s$" are absorption coefficients of the respective pigments, and "$s_1$", "$s_2$" ..., "$s_s$" are scattering coefficients of the respective pigments.

By means of the physical model, which is based on physical properties of respective color components of a paint formulation, it is possible to determine one or more characteristic variables which describe optical properties, such as spectral reflection, for example, of a paint formed on the basis of a respective paint formulation, or one or more respective optical constants of color components of a respective paint formulation, or a reflection spectrum of at least one or all color components of a respective paint formulation, or an absorption component K of the paint according to Kubelka-Munk or a scattering component S of the paint according to Kubelka-Munk.

The characteristic variables of the paint formulation or values thereof that are determined in the operative step 13 are supplied as input signals or input variables to a machine learner in the form of a neural network, i.e., to a neural network.

By means of the neural network, which has been trained on the basis of a multiplicity of known assignments of values of respective characteristic variables to texture parameters, texture parameters are assigned, according to a scheme determined during training, to the input characteristic variables or to the input values of the respective characteristic variables, in a calculation step 15. The texture parameters assigned by means of the neural network to the characteristic variables or to the input values of the characteristic variables are output in an output step 17 or stored in a memory. This means that by means of the method of the invention, texture parameters for a paint formulation can be determined or predicted without it being necessary for optical parameters of a paint corresponding to the paint formulation to be determined by means of a measuring instrument.

Because the texture parameters are determined on the basis of characteristic variables that describe optical properties of the paint formulation, the determination of the texture parameters, i.e., the assignment of the texture parameters to the characteristic variables or to respective values of the characteristic variables, takes place independently of specific individual constituents of the paint formulation 11, such as, for example, concentration details of color components—such as pigments, for example—that are needed for the mixing of a paint in accordance with the paint formulation. On the basis of this uncoupling of the determination of the texture parameters from individual color components of the paint formulation 11 and the concentrations thereof, the method of the invention can be executed by means of the same neural network, i.e., without any need for retraining of the neural network, even when color components of the paint formulation and/or concentrations thereof are modified.

The characteristic variables or values thereof that are passed on as input variables to the neural network describe optical properties of a paint and are determined as intermediate variables by means of a physical model from a respective paint formulation, such as, for example, the optical constants assigned to the respective paint formulation and/or the reflection parameters and/or absorption and/or scattering components calculated therefrom. On the basis of the characteristic variables based on optical properties, the input values passed on to the neural network, i.e., the respective values of the characteristic variables, can be reduced significantly in number relative to those of a neural network which assigns respective texture parameters of a paint formulation on the basis, as input variables, of all the color components used, and so a corresponding neural network is less complex and hence more efficient, i.e., more rapid and robust, thus being tolerant toward changes in, for example, a paint formulation, than a neural network formed with color components or concentrations of the color components as input values.

By means of the operative step 13 preceding the calculation step 15, the calculation step 15 is decoupled from individual constituents of the paint formulation 11. On account of this decoupling, changes in the paint formulation 11, owing to a deficiency in one pigment, for example, will not lead to any change in the neural network. If, for example, a color component of the originally mandated color formulation is absent, or if this component is replaced by a different color component, this is taken into account as early as in the operative step 13, in the calculation or determination of the optical properties of the respective color components and, on the basis thereof, of the value of the at least one characteristic variable of the amended paint formulation. Even if the value of the characteristic variable changes in this case, there is no change in the type or nature of the characteristic variable—whether, for example, it is an absorption component or a scattering component—that serves as input variable for the neural network. Accordingly, there is no need for the neural network to be reconfigured, and the only change, possibly, is the value of the corresponding input variable. In the calculation step 15, in spite of an amended paint formulation 11, this leads to correspondingly correct assignment of texture parameters, such as "sparkling intensity", a "sparkling area", or a distribution of graininess, i.e., a "graininess diffuse", for example.

The invention claimed is:

1. A method for predicting visual texture parameters of a paint having a known paint formulation, wherein the visual texture parameters of the paint are determined-using an artificial neural network on the basis of a number of color components used in the known paint formulation, the method comprising:

determining a value of at least one characteristic variable describing at least one optical property using a physical model for the known paint formulation, wherein the at least one optical property is selected from the group of optical properties consisting of a spectral reflection of a paint formed on a basis of a respective paint formulation, an optical constant of at least one color component of a respective paint formulation, a reflection spectrum predicted using a physical model for at least one color component of a respective paint formulation, an absorption component K according to Kubelka-Munk, a scattering component S according to Kubelka-Munk, and at least one optical characteristic variable calculated from respective optical constants of a number of color components of a respective paint formulation;

assigning the value to the known paint formulation;

transmitting the value to the artificial neural network as an input signal for determining the visual texture parameters, wherein the value determined and assigned to the known paint formulation describes the at least one optical property for at least some of the number of color components of the known paint formulation; and training the neural network using a plurality of color originals each having a respective known paint formulation, wherein for each of the plurality of color originals, a respective visual texture parameter is measured and assigned to a respective value of the at least one characteristic variable that is determined for the corresponding respective known paint formulation and which describes the at least one optical property for the respective known paint formulation.

2. The method as claimed in claim 1, wherein the input signal used comprises a scattering component and/or an absorption component and/or a spectral reflection of the paint that is calculated using the physical model.

3. The method as claimed in claim 1, further comprising:
determining, in an event a color component of the paint formulation of the paint is at least one of modified, replaced and removed, the visual texture parameters of the paint without renewed training of the neural network;
determining a new value of the at least one characteristic variable describing the at least one optical property for a new known paint formulation of the paint;
assigning the new value to the new known paint formulation; and
transmitting the new value to the neural network as a new input signal for determining the visual texture parameters, wherein the new value of the at least one characteristic variable describing the at least one optical property describes the at least one optical property for at least some of a number of color components of the new known paint formulation.

4. The method as claimed in claim 1, further comprising:
determining, for the respective known paint formulations, the respective value of the at least one characteristic variable using the physical model on the basis of parameters; and
measuring, using at least one sensor, of at least one color component of the number of color components used for the respective known paint formulation.

5. The method as claimed in claim 1, wherein a set of parameters that describes at least one optical property of at least some of the number of color components of a respective known paint formulation is selected as a characteristic variable.

6. The method as claimed in claim 1, wherein the at least one optical characteristic variable calculated from the respective optical constants of the number of color components of a respective paint formulation is a weighted average of respective absorption and scattering coefficients of the number of color components of the respective paint formulation.

7. The method as claimed in claim 1, further comprising:
predicting a color space coordinate derived from the reflection spectrum of the at least one color component of the respective paint formulation using the physical model; and
selecting the color space coordinate as the at least one optical property.

8. The method as claimed in claim 1, wherein the visual texture parameters are selected from the group consisting of sparkle intensity, sparkle area, distribution of graininess, and combinations thereof.

9. The method as claimed in claim 1, wherein a paint formulation for a paint is decided using texture parameters predicted for a plurality of known paint formulations, wherein the texture parameters display a least-possible deviation from respective texture parameters of a mandated target paint.

10. A computer program product comprising a non-transitory computer usable storage medium and a computer program stored on the non-transitory computer usable storage medium and having program code means configured to execute all computer-implemented steps of the method as claimed in claim 1, wherein the computer program is run on an arithmetic unit.

11. The computer program product as claimed in claim 10, wherein the computer program is stored on a computer-readable data carrier.

* * * * *